United States Patent [19]

Imai et al.

[11] Patent Number: 5,232,942

[45] Date of Patent: Aug. 3, 1993

[54] Q-2819 SUBSTANCE AND THE USE THEREOF

[75] Inventors: Harumitsu Imai, Kanagawa; Hidenori Yazawa, Tokyo; Koji Nagai, Tokyo; Takeshi Saito, Tokyo, all of Japan; Shu Fang Liang, Shanghai, China

[73] Assignee: Yamanouchi Pharmaceutical Co., Ltd., Tokyo, Japan

[21] Appl. No.: 582,860

[22] PCT Filed: Apr. 13, 1989

[86] PCT No.: PCT/JP89/00402

§ 371 Date: Nov. 29, 1990

§ 102(e) Date: Nov. 29, 1990

[87] PCT Pub. No.: WO89/09769

PCT Pub. Date: Oct. 19, 1989

[30] Foreign Application Priority Data

Apr. 14, 1988 [JP] Japan .................. 63-92572

[51] Int. Cl.⁵ .................. A61K 31/35; C07D 311/92
[52] U.S. Cl. .................. 514/455; 549/280
[58] Field of Search .................. 514/455; 549/280

[56] References Cited

U.S. PATENT DOCUMENTS 4,547,579 10/1985 Möckli .................. 549/280
4,939,274 7/1990 Terao et al. .................. 549/315
4,963,581 10/1990 Kanamaru et al. .................. 514/455

OTHER PUBLICATIONS

Imai, II et al "Substance Q-2819 and its Preparation from Chrysosporium" CA 113:57452e,
Leeper, F. J. et al "Biomimetic Syntheses of Polyketide Aromatics from Reaction of an Orsellinate Anion with Pyrones and Pyrylium Salt" J. Chem. Soc. Perkin Trans (1984) pp. 1053-1059.

Primary Examiner—C. Warren Ivy
Assistant Examiner—A. A. Owens
Attorney, Agent, or Firm—Burgess, Ryan & Wayne

[57] ABSTRACT

The present invention relates to Q-2819 substance represented by formula described below and a process for production thereof as well as a novel microorganism capable of producing the substance:

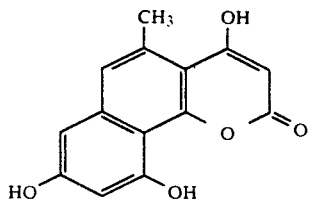

18 Claims, 8 Drawing Sheets

Q-2819 SUBSTANCE AND THE USE THEREOF

FIELD OF THE INVENTION

The present invention relates to Q-2819 substance and a process for production thereof as well as bacterial strains capable of producing the same.

Q-2819 substance removes active oxygen seeds in the living body and exhibits an action of preventing or reducing the formation of lipid peroxides and is thus useful as a drug for the treatment of various diseases supposed to be induced by these active oxygen seeds.

BACKGROUND

Oxygen is necessary and indispensable for maintaining life such as energy production, metabolism, etc. in the living body. Oxygen becomes a so-called active oxygen seed such as a hydrogen anion radical, hydrogen peroxide, a hydroxy radical, etc. in energy-producing reactions, enzyme reactions or reactions with ultraviolet rays or radiations. The active oxygen seed is useful for the living body in oxygen-added enzyme, a sterilizing action of leucocytes, etc. on one hand but on the other hand, accelerates conversion into peroxides of unsaturated fatty acids constructing phospholipids of biomembrane such as oleic acid, linoleic acid, linolenic acid, arachidoic acid, etc. which are abundantly present in the living body. The lipid peroxides induce alkoxy radicals or hydroxy radical, attack biomembrane and cause impairment of membrane or inactivation of various useful enzymes (Metabolism, 15 (10), special 1978 edition featuring active oxygen).

However, enzymes such as superoxide dismutase (SOD), catalase, glutathione peroxidase, etc. participate in metabolic inactivation of the active oxygen seeds described above, and a variety of vitamins having an antioxidizing activity including α-tocopherol (vitamin E) and the like, in the living body. By these actions, the living body is normally maintained. However, it is often recognized that, by some reason, defects are caused in adequate protection mechanisms by these substances, active oxygenseeds beyond the ability of these protection mechanisms generate, or formation and accumulation of lipid peroxides occur. Where defects or the like are caused in such protection mechanisms, peroxidation proceeds like a chain reaction to induce various serious disturbances in the living body. Representative examples of these disturbances are various diseases caused by platelet coagulation, inflammation, hepatic disturbances, arteriosclerosis, hemolysis, senility or senile diseases, retinal diseases, cardiac and pulmonary disturbances induced by certain drugs, ischemic vascular diseases, ischemic cardiac diseases, organ disturbances in ischemia-recycling, etc. Experimental Medicine, 4 (12), special 1986 edition featuring in vivo free radical and disease.

In general, drugs having an antioxidizing action have been developed for purposes of preventing and treating the diseases described above.

For example, in Japanese patent application laid-open No. 63-152374, hydroxybutenolide derivatives having an action of eliminating active oxygen seeds and organic radicalseeds are disclosed and it is described there that the derivatives have an effect of treating, preventing and improving various disturbances such as ischemic cardiac function disturbances, ischemic cerebral function disturbances, ischemic renal disturbances, etc.

The compound of the present invention has an action of inhibiting formation of lipid peroxides and an action of scavenging superoxide anion radicals and is useful as a prophylactic and therapeutic drug for the aforesaid various diseases.

Specific examples of diseases to which the compound is applied include an agent for improving organs of the circulatory system such as an anti-arrhythmic agent, an anti-myocardial infarction agent, an agent for preventing from growing senile or senile dementia, treatment or improvement after subarachnoid hemorrhage, etc.; an agent for improving renal function, an agent for treating stress-induced digestive ulcer, an anti-arteriosclerotic agent, an antiinflammatory agent, an agent for preventing platelet coagulation, an agent for treating autoimmune diseases, an anti-rheumatoid agent, an anti-sclerodermic agent, an anti-pulmonary fibrosis agent, an anti-retinitis agent, an agent for preventing and treating cataract, etc.

SUMMARY OF THE INVENTION

The present invention relates to a substance referred to herein as Q-2819 and a process for producing the substance as well as a microorganism capable of producing the substance.

The compound, Q-2819 substance, of the present invention is a compound specified by the following physicochemical, properties and chemical structure of formula (I).

Chemical structure:

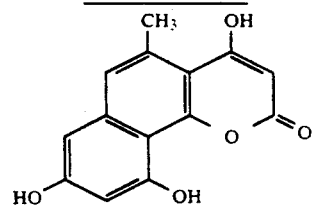

(I)

| Physicochemical properties: | Q-2819 Substance |
|---|---|
| (1) UV spectrum | FIG. 1 (in methanol) |
| (2) IR spectrum | FIG. 2 (KBr tablet) |
| (3) $^1$H-NMR spectrum | FIG. 3 (DMSO-$d_6$, 500 Mz) |
| (4) $^{13}$C-NMR spectrum | FIG. 4 (DMSO-$d_6$, 125 Mz) |
| (5) Mass spectrum (EI-MS) | FIG. 5 258 (M$^-$) |
| (6) Molecular weight | 258 |
| (7) Molecular formula | $C_{14}H_{10}O_5$ |
| (8) Appearance | light yellow needles |
| (9) Melting point | 275–280° C. |
| (10) Specific rotation $[\alpha]_D^{22}$ | 0° (C1, DMSO) |
| (11) Basic, neutral or acidic property | acidic substance |
| (12) Solubility | soluble in DMSO, pyridine or alkali water; sparingly soluble in methanol, ethanol, acetone, acetonitrile or ethyl acetate; insoluble in water, chloroform, benzene or hexane |
| (13) Thin layer chromatography [silica gel 60 F$_{254}$ was used, detected at 254 nm with UV lamp] | ⋄ Rf = 0.32 (chloroform:methanol = 5:1) ⋄ Rf = 0.26 (ethyl acetate:methanol = ⋄ Rf = 0.63 (chloroform:methanol: acetic acid = 10:2:0.1) |

As is clear from the chemical structure described above, Q-2819 substance can be present, as the following two tautomeric isomers of formula (II) and (III) in addition to formula (I) described above:

(II)

(III)

Furthermore, these compounds are acidic substances and form salts. As the salts, there are alkali metal salts and basic amino acid salts. Examples of the alkali metal salts are sodium salt, potassium salt, etc. Examples of the basic amino acid salts are arginine salt, lysine salt, ornithine salt, etc.

The desired compound of the present invention also includes the isomers described above and salts thereof.

BEST MODE FOR PRACTICING THE INVENTION

The activity of Q-2819 substance of the present invention for scavenging active oxygen seeds is shown together with a method for measurement.

(A) Measurement of superoxide anion scavenging activity

Method

The superoxide anion scavenging activity of the compound (Q-2819) of the present invention was determined by the method of McCord and Fridovich (J. Biol Chem., 244 (22), 6049-6055, 1969). That is, xanthine oxidase was added to $5 \times 10^{3 1 2}$ M potassium phosphate buffer (pH 7.8) containing $1 \times 10^{-4}$ M EDTA, $1 \times 10^{-5}$ M ferricytochrome C and $5 \times 10^{-5}$ M xanthine in such a manner that the increment of absorbance at 550 nm became 0.025 per minute at 25° C., which was made the reaction system. It is defined that one unit of SOD activity is 50% inhibitory activity of the increment in absorbance at 550 nm in this reaction system. The superoxide anion scavenging activity of the compound of the present invention is expressed by a concentration showing activity of one unit of SOD.

Results

Figure 6:
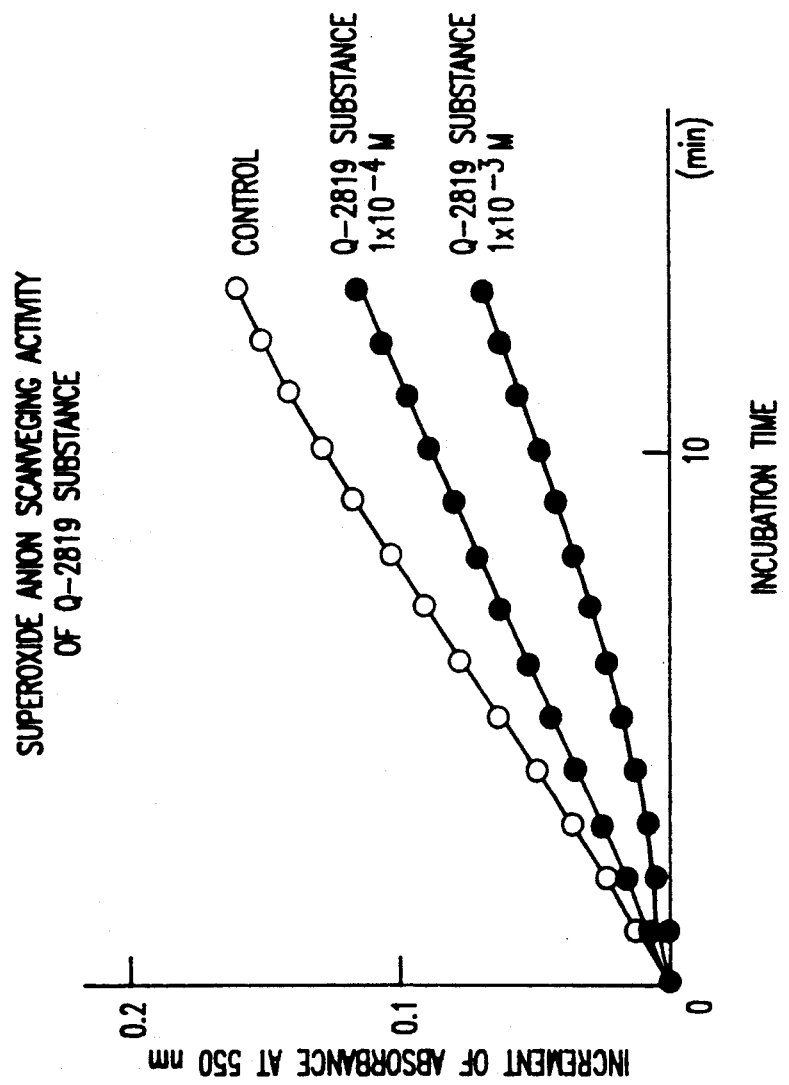
FIG. 6 shows superoxide anion scavenging activity of Q-2819 substance.

As shown in FIG. 6, Q-2819 substance showed the superoxide anion scavenging activity. Furthermore, Q-2819 substance showed activity equivalent to enzyme activity of 1 unit of SOD, in $3.8 \times 10^{-4}$ M.

(B) Measurement of antioxidation activity

Method

Substances generally called antioxidants have an activity of decoloring 1,1-diphenyl-2-picrylhydrazyl (DPPH) which is a stable radical. Therefore, the antioxidation activity of the compound (Q-2819) of the present invention was determined as follows according to the method of Blois (Nature, 181, 1199-1200, 1958).

Figure 7:
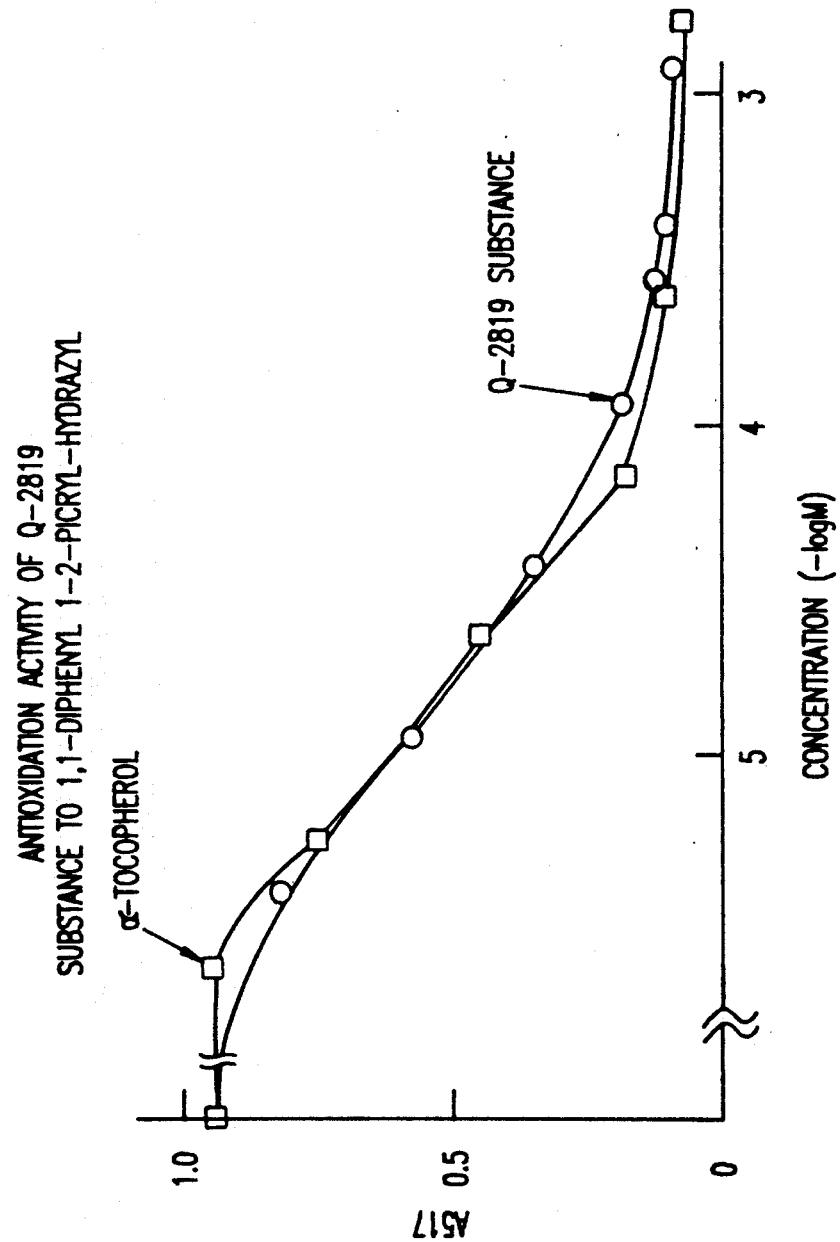
FIG. 7 shows an antioxidation activity of Q-2819 substance.

That is, DPPH was dissolved in ethanol in a concentration of 0.1 mM and the solution was mixed with a test compound. Thirty minutes after, absorbance was measured at 517 nm. The results are shown in FIG. 7.

Q-2819 had an antioxidation ability almost comparable to that of α-tocopherol.

(C) Measurement of activity of inhibiting formation of lipid peroxides

Method

The cerebral cortex was ectomized from a Wistar strain male rat (weighing 200 g) and 50-fold amount of ice-cooled 50 mM Tris-HCl buffer (pH 7.7) was added thereto. The mixture was homogenized to prepare a tissue homogenate. A ferric chloride solution was added to the tissue homogenate to form lipid peroxides. Lipid peroxides were quantitatively determined with thiobartituric acid (TBA) according to the method of Yagi (Vitamin, 37, 105-112, 1968).

Figure 8:
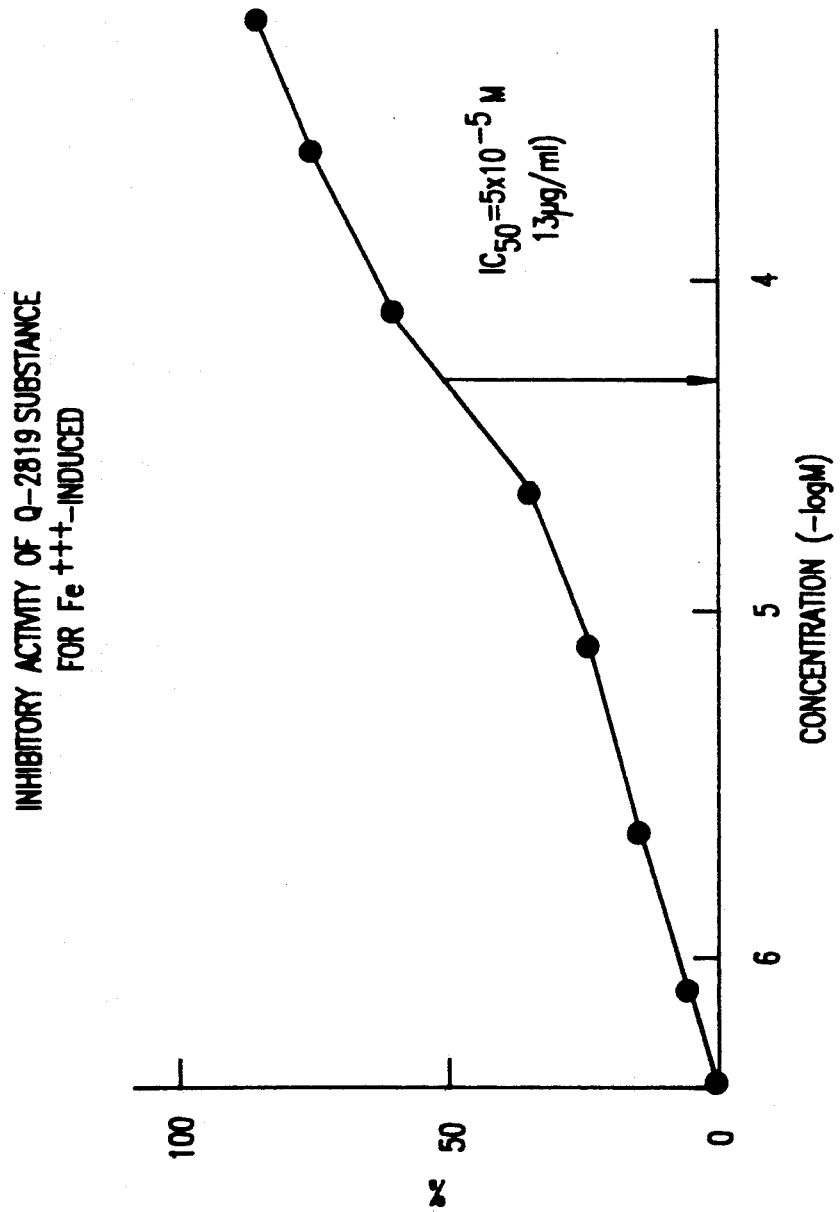
FIG. 8 shows an inhibitory activity of Q-2819 substance for $Fe^{+++}$-induced lipid peroxides.

The results are shown in FIG. 8.

The compound (Q-2819) of the present invention inhibited peroxidation of Fe-induced lipids in $IC_{50} = 5 \times 10^{-5}$ M.

The compound of the present invention may be mixed with conventional pharmaceutically acceptable carriers, excipients, diluting agents, etc. and prepared into medical compositions e.g., tablet, capsule (including soft capsule and microcapsule), liquid, suppository, injection, pernasal agent. These medical compositions may be safely administered orally or parenterally. A dose may vary depending upon patients to be administered, symptom, route for administration, etc. but where the composition is orally administered to mammal, a unit dose may generally be, when calculated as Compound (I), approximately 0.1 mg/kg to 100 mg/kg body weight, preferably approximately 0.5 mg/kg to 50 mg/kg body weight, once to about 3 times a day.

Further where the composition is parenterally administered, it may be administered, for example, in the case of suppository, in a dose of approximately 5 mg to 10 mg/kg when calculated as Compound (I) once or twice a day; in the case of injection, approximately 0.1 mg/kg to 10 mg/kg when calculated as Compound (I) once or twice a day.

In preparing the oral preparations, e.g., tablets, described above, binders (e.g., hydroxypropyl cellulose, hydroxymethylpropylmethyl cellulose, macrogol, etc.), disintegrators (e.g., starch, calcium carboxymethyl cellulose, etc.), excipients (e.g., lactose, starch, etc.), lubricants (e.g., magnesium stearate, talc, etc.), and the like may be appropriately formulated.

Furthermore in preparing the parenteral preparations, e.g., injection, isotonic agents (e.g., glucose, D-sorbitol, D-mannitol, sodium chloride, etc.), preservatives (e.g., benzyl alcohol, chlorobutanol, methyl p-oxybenzoate, propyl p-oxybenzoate, etc.), buffers (e.g., phosphate buffer, sodium acetate buffer; etc.) and the like may be appropriately formulated.

Since the compound of the present invention is sparingly soluble in water when it does not form any salt, dissolution aids (e.g., polyvinyl pyrrolidone, triacetyne, propylene glycol, etc.) may be formulated, if necessary.

The Q-2819 substance can be produced by culturing Q-2819-producing bacteria belonging to the genus Chrysosporium, accumulating Q-2819 substance in medium and collecting the substance from the medium. An example of bacteria belonging to the genus Chrysosporium which can be used in the present invention is Chrysosporium sp. Q-2819 strain isolated from a soil sample collected in cedar forest in a pavk at Beijin, People's Republic of China. Morphological and physiological properties of this strain are as described below.

The strain is classified in Fungi Imperfect in which development of perfect stage is not observed in various media and which forms conidia on the conidiophore separated from aerial mycelium. The aerioal mycelium is 50 $\mu$m long, 0.5 to 2 $\mu$m wide, hyaline smooth walled and has septum. The branches arise at acute angles and whirled once and/or twice to form dendritic structure. The conidiophore is not clearly distinguishable from aerial mycelium. The conidia are formed terminally on the mycelia and the intercalarycanidia also formed, in which 2 to 4 cionidia are often formed on the other branches. It is also observed that conidia are formed terminally on short branches arisen on the side of mycelium.

The conidia are single cellse hyaline or subhyaline, echinulate, subspherical to clavate and a size of 3 to 4.5 $\mu$m $\times$ 1.5 to 2.5 $\mu$m. The intercalary conidia have a barrel shape with the both ends being cut-like and are wider than the mycelia. No chlamidospore is formed.

Colony on maltose-agar medium reaches 2.5 cm in diameter at 24° C. in 2 to 3 weeks. It is not so spread but raised with tufts of mycelia. The surface is powdery to felty. Color of colony changes white and to pinkish light brown during the cultivation. Color of the reverse side is yellow brown. Colony on potato dextrose-agar medium is different from the colony on maltose-agar medium in exhibiting greyish green in 2 to 3 weeks and diffusing yellow brown pigment in medium.

Thus, the strain has been identified to belong to the genus Chrysosporium and has been named Chrysosporium sp. Q-2819. This strain has been deposited in the Fermentation Research Institute of the Agency of Industrial Science and Technology of Japan *1 under FERM BP-2370 *2. The strain was imported from the People's Republic of China via the Yokohama Plant Quarantine Station under Admission No. 62 Yoko Shoku 522 pursuant to Instructions of the Ministry of Agriculture, Forestry and Fisheries.

*1: at No. 1-3, Higashi 1-chome, Tsukuba-shi Ibaragi-ken, Japan (post Code 305)
*2: on Mar. 10, 1988

The Chrysosporium sp. Q-2819 strain of the present invention also includes, in addition to strain isolated from the natural world, artificial mutants with ultraviolet rays, x rays, chemicals, etc. and natural variants thereof.

In the present invention, the Q-2819 substance-producing bacteria belonging to the genus Chrysosporium is cultured in a manner similar to a method for culturing ordinary microorganisms but deep culture in liquid medium is generally advantageous. As the medium used for culture, any medium is usable so long as it contains nutrient sources utilized by the producing bacteria. That is, synthetic medium, semi-synthetic medium or natural medium can be used. In composition of the medium, for example, as carbon sources, there may be used D-xylose, glucose, D-fructose, L-ramnose, mannitol, glycerine, dextrin, starch, vegetable oil, etc.; as nitrogen sources there may be used meat extract, peptone, gluten meal, cotton seed oil, soybean meal, peanut meal, fish meal, corn steep liquor, dried yeast, yeast extract, ammonium sulfate, ammonium nitrate, urea and other organic or inorganic nitrogen courses. Further as metal salts, sulfates, nitrates, chlorides, carbonates, phosphates, etc. of Na, K, Mg, Ca, Zn, Fe, etc. may be supplemented, depending upon necessity. Further if necessary, antibiotic production accelerators or defoaming agents such as methionine, cystein, cystine, methyl oleate, lard, silicone oil, surface active agents, etc. may also used appropriately.

It is generally advantageous for culture conditions to culture under aerobic conditions. A temperature for culture is desirably in a range of from approximately 18° to 28° C., preferably at about 25° C. Good results can be obtained when a pH value of the medium maintained between approximately 5 and 10, preferably in a range of from about 6 to about 8. A period for incubation may vary depending upon composition of the medium, temperature, etc. but is generally about 1 to about 5 days. At completion of the culture, the desired substance is selectively accumulated.

In order to isolate and collect the product of the present invention from the culture, a method for isolating antibiotic from ordinary culture is applied. Since Q-2819 substance is contained in the cultured medium, the cells are removed by centrifugation or filtration and the effective substance is then extracted from the filtrate. That is, isolation, collection and purification can be performed by means applied to the preparation of ordinary antibiotics utilizing a difference in solubilizing property and solubility in an appropriate solvent, a difference in crystalizing property and crystalizing rate from a solution, a difference in adsorption affinity to various adsorbents, a difference in distribution between 2 liquid phases, etc. Depending upon necessity, the method is used singly, in combination of optional order or repeatedly.

Next, the present invention is described in more detail by referring to the examples below. The method of preparation in accordance with the present invention has been described hereinabove and is described in more detail by referring to the examples below.

EXAMPLE

Medium containing 1.0% of glucose, 2.0% of potato starch, 0.5% of yeast extract, 0.5% of polypeptone and 0.4% of calcium carbonate (pH 7.0) was prepared and 60 ml each of the medium was separately charged in an Erlenmeyer's flask of 500 ml volume followed by sterilization at 120° C. for 20 minutes. Myçelia of Chrysosporium sp. Q-2819 strain grown on Bennett's agar medium were scraped out and inoculated on the above medium. Shake culture was conducted at 28° C. for 3 days to prepare a seed medium. Next, 2 l of medium having the same composition as described above was prepared and 100 ml each of the medium was separately charged in an Erlenmeyer's flask of 500 ml volume followed by sterilization at 120° C. for 20 minutes. The seed medium was inoculated on the above medium at a rate of 3.0%. Shake culture was continued at 28° C. for 5 days. After a pH value of the cultured medium was adjusted to 8.5, Radiolite #600 (manufactured by Showa Chemical Industry Co., Ltd.) was added thereto. After stirring, the mixture was filtered to give 1.6 liters of the filtrate. After pH of the filtrate was adjusted to 4.5, 2.5 liters of ethyl acetate was added thereto followed by thorough agitation. The ethyl acetate phase was separated and anhydrous sodium sulfate was added thereto to dehydrate. The dehydrated ethyl acetate phase was concentrated under reduced pressure to give 420 mg of brown powders. After 420 mg of the brown powders was dissolved in a small quantity of solvent mixture of chloroform:methanol (25:1), the solution was applied to a column packed with 10 g of Wakogel C-200 (manufactured by Wako Pure Chemical Industry Co., Ltd.) using the aforesaid solvent mixture, and column chromatography was performed using the same solvent mixture as a developing solvent. For detection of Q-2819 substance, silica gel thin layer chromatography was utilized. That is, each fraction of the eluate in the column chromatography was spotted on TLC plate [silica gel 60F. (manufactured by Merck Inc.)]. The TLC plate was developed with a solvent mixture of chloroform:methanol (5:1). Q-2819 substance showing Rf of 0.32 with UV lamp (254 nm) and showing SOD-like activity was detected. The fraction of column chromatography in which Q-2819 substance alone is present is collected. Concentration under reduced pressure gave 120 mg of Q-2819 substance as light yellow powders. The light yellow powder was dissolved in a small quantity of ethyl acetate with heating and the solution was allowed to cool to give Q-2819 substance as light yellow needles.

We claim:

1. A compound having the formula shown below and tautomeric isomers and salts thereof.

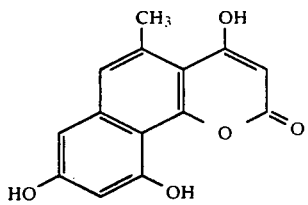

Figure 1:
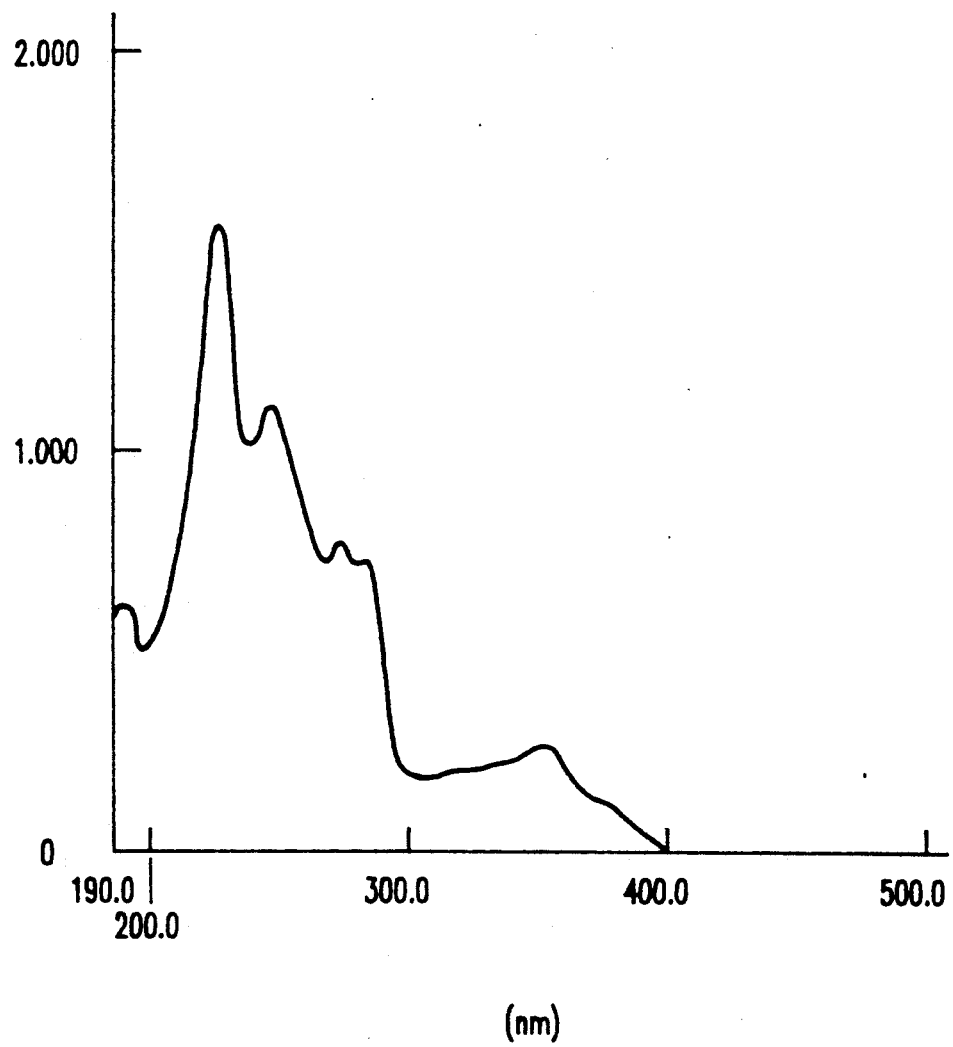
FIG. 1 shows UV spectrum of Q-2819 substance.

2. The compound of claim 1 having the UV spectrum shown in FIG. 1.

Figure 2:
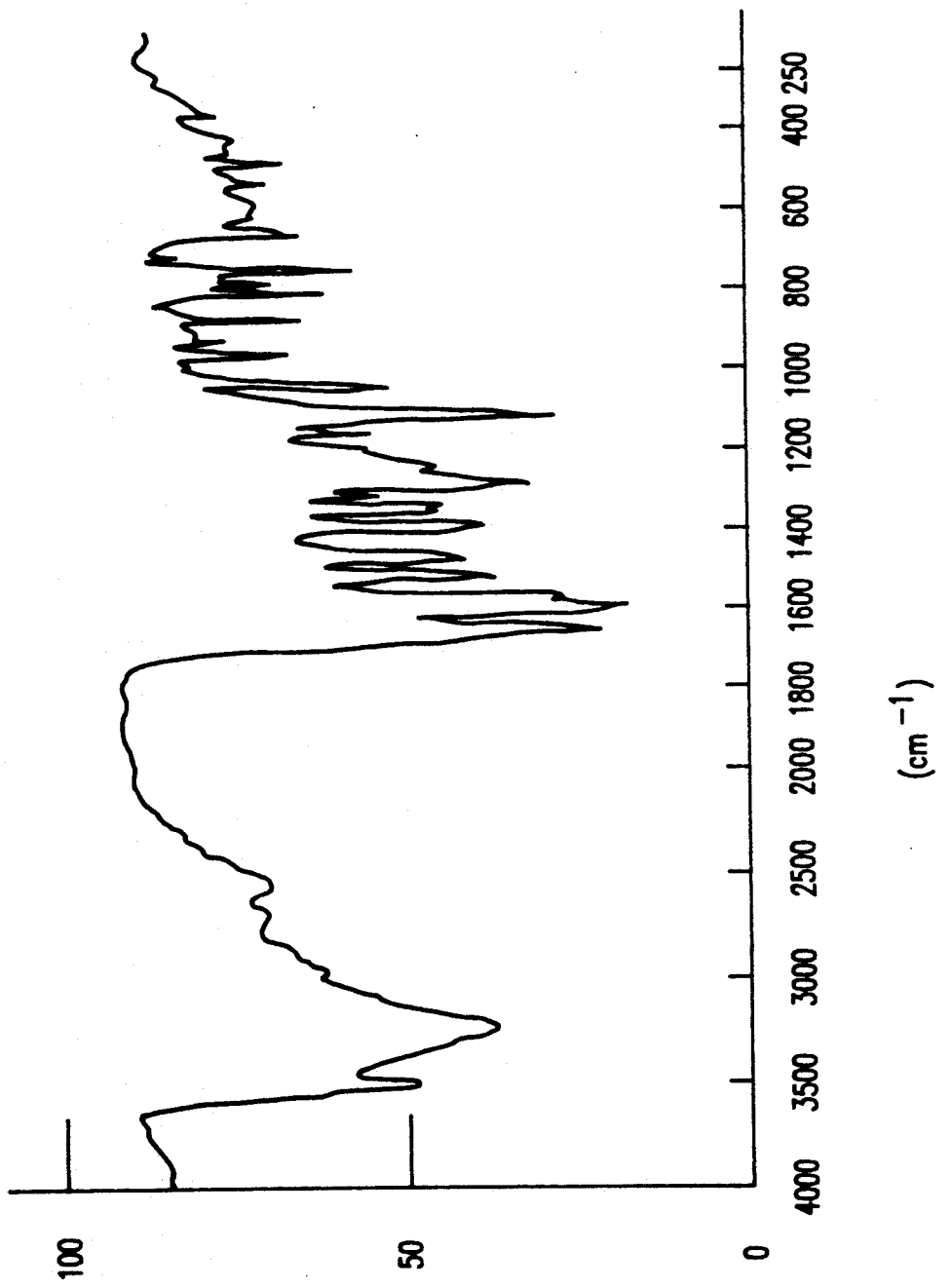
FIG. 2 shows IR spectrum of Q-2819 substance.

3. The compound of claim 1 having the IR spectrum shown in FIG. 2.

Figure 3:
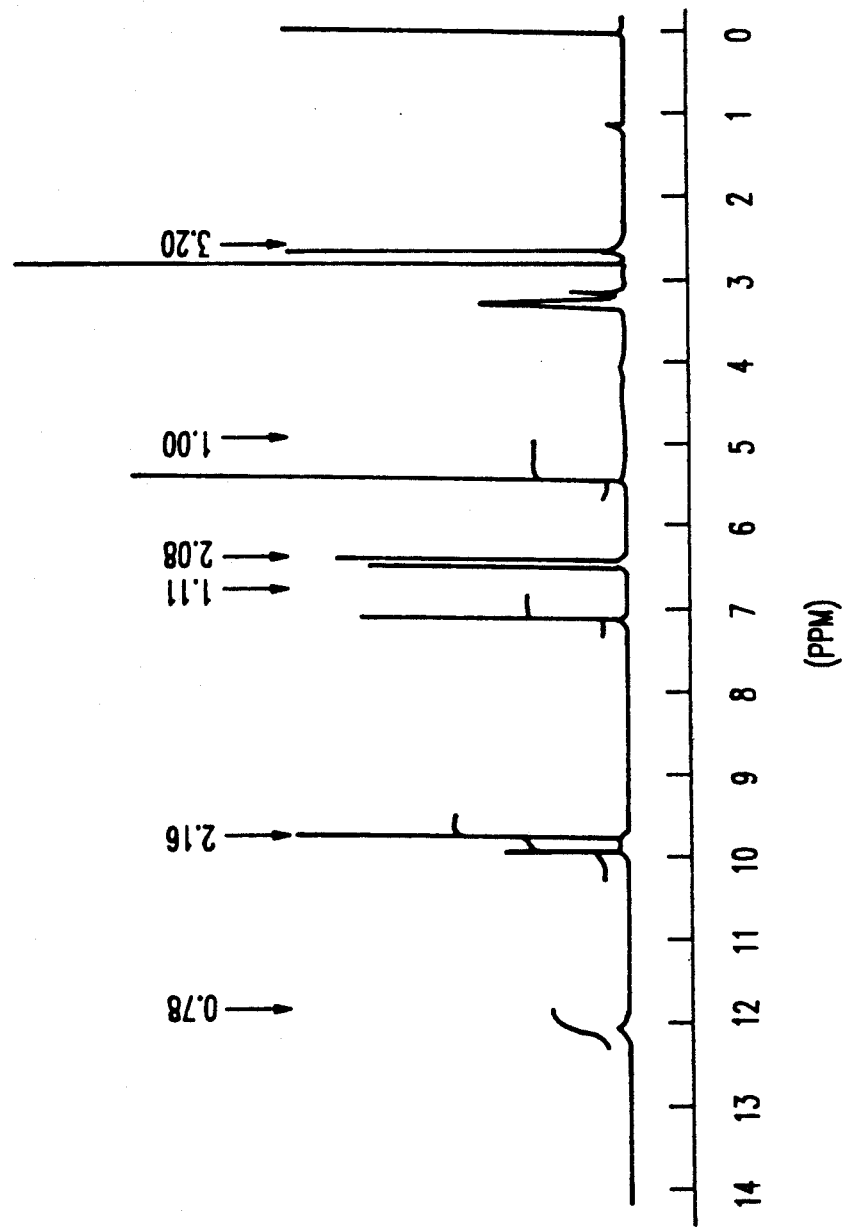
FIG. 3 shows $^1$H-NMR spectrum of Q-2819 substance.

4. The compound of claim 1 having the $^1$H-NMR spectrum shown in FIG. 3.

Figure 4:
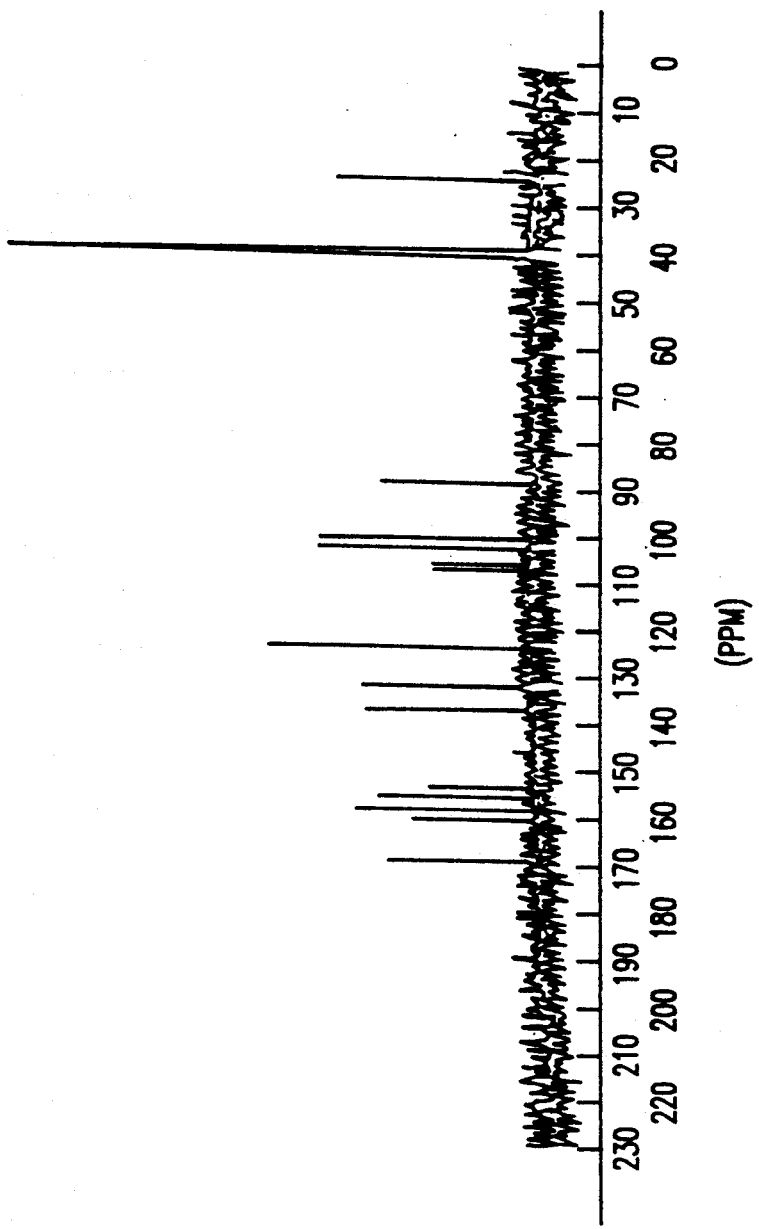
FIG. 4 shows $^{13}$C-NMR spectrum of Q-2819 substance.

5. The compound of claim 1 having the $^{13}$C-NMR spectrum shown in FIG. 4.

Figure 5:
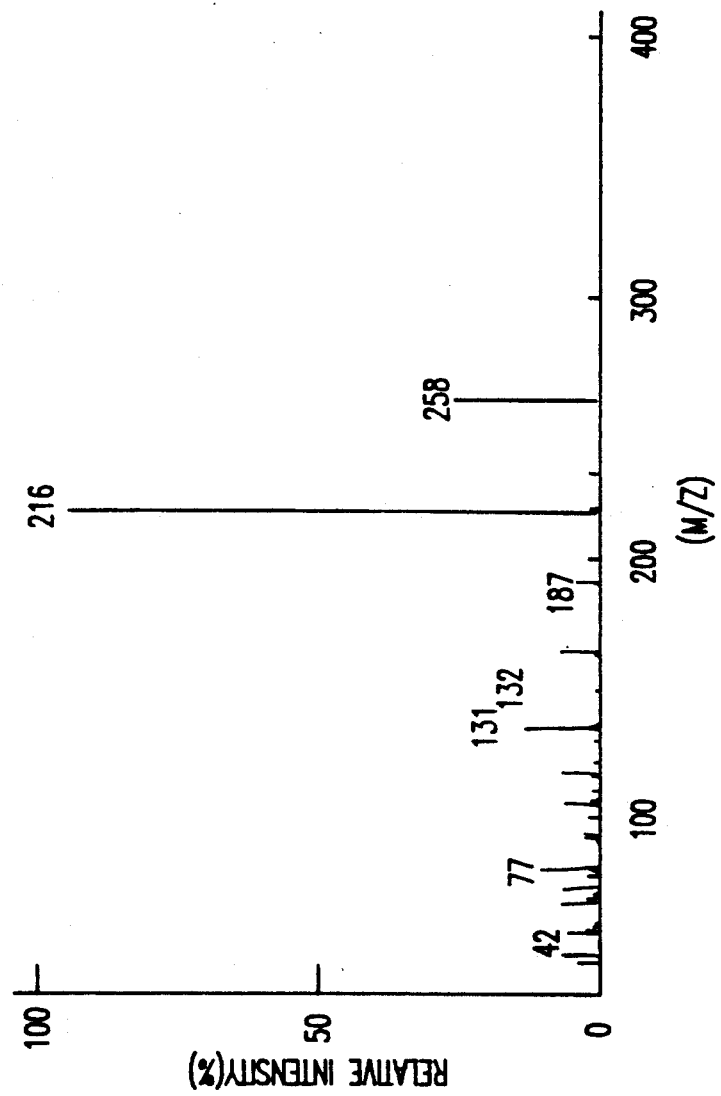
FIG. 5 shows mass spectrum of Q-2819 substance.

6. The compound of claim 1 having the mass spectrum shown in FIG. 5.

7. The compound of claim 1 wherein the salts are selected from alkali metal salts and basic amino acid salts.

8. The compound of claim 1 wherein the tautomers are selected from compounds having the formulas II and II shown below:

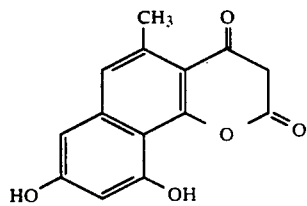 (II)

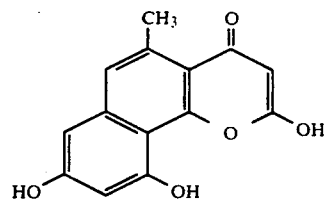 (III)

9. A composition for controlling the content of oxygen seeds in the body comprising a compound having the structure shown below, tautomeric isomers and salts thereof in combination with a pharmaceutically acceptable carrier.

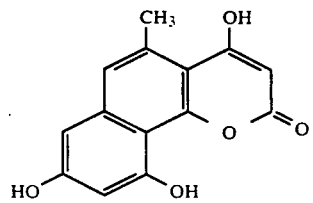

10. The compound of claim 9 containing from 0.1 to 100 mg/kg of body weight of said compound.

11. The compound of claim 9 wherein the salts are selected from alkali metal salts and basic amino acid salts.

12. The compound of claim 9 wherein the tautomers have the formulas shown below:

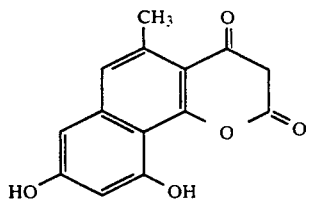 (II)

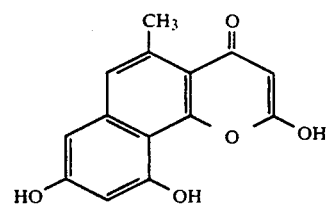 (III)

13. A method for controlling the content of oxygen seeds in the body of a warm blooded animal comprising administering to said warm blooded animal the composition of claim 9.

14. The composition of claim 13 comprising administering the composition orally at the rate of 0.1 to 100 mg/kg body weight once to about three times per day.

15. The method of claim 13 comprising administering the composition orally at the rate of 0.5 to 50 mg/kg body weight once to about three times per day.

16. The composition of claim 13 comprising administering the composition parenterally at the rate of 0.1 to 10 mg/kg of body weight once or twice per day.

17. The method of claim 13 comprising administering the composition as a suppository at the rate of 5 to 10 mg/kg of body weight once or twice per day.

18. The method of claim 13 comprising administering the composition by injection at the rate of 0.1 to 10 mg/kg of body weight once to twice per day.

* * * * *